(12) United States Patent
Barongan (10) Patent No.: US 8,876,882 B2
(45) Date of Patent: Nov. 4, 2014

(54) CUTTING STENT

(76) Inventor: Mark Gelido Barongan, San Diego, CA (US)

( * ) Notice: Subject to any disclaimer, the term of this patent is extended or adjusted under 35 U.S.C. 154(b) by 387 days.

(21) Appl. No.: 10/962,279

(22) Filed: Oct. 9, 2004

(65) Prior Publication Data

US 2005/0080478 A1    Apr. 14, 2005

Related U.S. Application Data

(60) Provisional application No. 60/510,114, filed on Oct. 10, 2003.

(51) Int. Cl.
*A61F 2/06* (2013.01)
*A61F 2/86* (2013.01)
*A61B 17/3207* (2006.01)
*A61B 17/00* (2006.01)
*A61F 2/07* (2013.01)
*A61F 2/848* (2013.01)

(52) U.S. Cl.
CPC ........... *A61F 2/86* (2013.01); *A61B 17/320725* (2013.01); *A61B 17/320758* (2013.01); *A61B 2017/00353* (2013.01); *A61F 2/07* (2013.01); *A61F 2/848* (2013.01); *A61F 2220/0016* (2013.01); *A61F 2230/005* (2013.01)
USPC ..................................................... 623/1.14

(58) Field of Classification Search
USPC ............. 623/1.14–1.15, 1.2, 1.28, 1.29, 1.32, 623/1.36, 1.13, 1.11, 1.12; 606/159, 194, 606/108, 198
See application file for complete search history.

(56) References Cited

U.S. PATENT DOCUMENTS

| | | | | |
|---|---|---|---|---|
| 5,167,614 A * | 12/1992 | Tessmann et al. | ........... | 623/1.15 |
| 5,176,626 A * | 1/1993 | Soehendra | ........................ | 604/8 |
| 5,397,355 A * | 3/1995 | Marin et al. | ................... | 623/1.2 |
| 5,593,417 A * | 1/1997 | Rhodes | ........................ | 623/1.14 |
| 5,797,935 A * | 8/1998 | Barath | ......................... | 606/159 |
| 5,853,419 A * | 12/1998 | Imran | ........................ | 623/1.15 |
| 6,197,013 B1 * | 3/2001 | Reed et al. | .................... | 604/509 |
| 6,383,171 B1 * | 5/2002 | Gifford et al. | ................ | 604/508 |
| 6,451,051 B2 * | 9/2002 | Drasler et al. | ............... | 623/1.15 |
| 6,632,231 B2 * | 10/2003 | Radisch, Jr. | .................. | 606/159 |
| 6,827,734 B2 * | 12/2004 | Fariabi | ........................ | 623/1.18 |
| 7,731,744 B1 * | 6/2010 | Cox | ............................. | 623/1.14 |
| 2001/0010014 A1 * | 7/2001 | Trozera | ........................ | 623/1.16 |
| 2004/0133223 A1 * | 7/2004 | Weber | ............................ | 606/159 |
| 2004/0215223 A1 * | 10/2004 | Shaw et al. | ................... | 606/170 |

* cited by examiner

*Primary Examiner* — Katherine Dowe
(74) *Attorney, Agent, or Firm* — Valauskas Corder LLC (57) ABSTRACT

This invention is a stent that has cutting bars or blades in the direction of the balloon and longitudinally at five equidistant points along the direction of the stent's body. There are two patterns in this invention. The first pattern has five blades equidistant from the other and run longitudinally along the direction of the stent body and the other pattern has five shorter blades equidistant from the other to constitute one set. Each set is arranged in a staggered pattern from the next set. Furthermore, the edges of stent's blades or bars are angular or beveled and integrated into a stent strut pattern in order to facilitate the entry of blades into a blockage caused by calcium, plaque and/or debris.

19 Claims, 12 Drawing Sheets

CUTTING STENT

CROSS-REFERENCE TO RELATED APPLICATIONS

This application claims priority to Provisional Application No. 60/510,114 filed Oct. 10, 2003.

FEDERALLY SPONSORED RESEARCH

Not Applicable

TECHNICAL FIELD OF INVENTION

This invention is a stent for intravascular procedures that replaces the application of a cutting balloon in order to facilitate the placement of the stent in a blood vessel blockage.

BACKGROUND OF INVENTION

Intravascular stents are commonly used to maintain patency, opening or spread, of a blood vessel in an attempt to maintain normal blood flow in situation such as stenosis, a constriction of blood vessels due to plaque, calcium, thrombus, and other debris or combination of these. Intravascular stents are typically metallic and self-expanding or balloon expandable. However, cases where the blockage, which is composed of plaque, calcium, and other calculus debris, is severe, cutting into the blockage is required in order to enable the delivery and placement of the stent.

A conventional method for placing a stent into an artery with calcium, plaque, and debris is performed by the following process. The process starts by engaging a guiding catheter into the opening of a blood vessel. Then, a guidewire is chosen to pass through the blood vessel to its distal portion of the vessel. A balloon with surgical blades is then advanced over the wire and placed at the site of the stenosis, blockage or obstruction. The balloon with surgical blades is then inflated using an inflation device. The blades will score the plaque, calcium, and debris that line the intimal wall of the artery. Once a satisfactory scoring of the lumen is achieved, the balloon with surgical blades is then withdrawn into the guiding catheter and taken out over the guidewire.

To prevent collapsing of the plaque debris into the freshly cut area, a stent is chosen to act as internal scaffolding to help bridge the brittle and loose debris. A metal stent is then placed into the freshly cut area by use of the coronary guidewire. A stent of specific size is chosen to match the blood vessel size. Then, stent is inflated using an inflation device. The stent is inflated to its nominal size (the size chosen to match the vessel caliber). Since the stent is mounted to an angioplasty balloon, the stent will expand to a specific size based on what atmosphere the stent balloon is inflated to.

Then, the stent may be post-dilated using a non-compliant angioplasty balloon to ensure good apposition to the blood vessel wall. The post-dilation balloon is taken to slightly higher atmospheric pressures using a balloon inflation device. After a satisfactory lumen size is achieved, and then the post-dilation balloon can be withdrawn into the guiding catheter.

However, using the cutting balloon to cut into the blockage can sometimes lead to serious consequences. A common problem with this procedure is the likelihood of small plaque and debris that are dislodged in the distal blood vessel causing flow obstruction and/or pain for the patient. The debris will float down the artery and block blood flow or cause chest pain. Part of the cause of falling debris in the blood stream is due to the blade edge scoring the intimal wall. This scoring of the intimal wall is accomplished by physically inflating a balloon that has mounted athrotomes or linear and narrow surgical blades on the balloon that when pushed radially outward, expanding the balloon, causes a linear crack or score parallel to the intimal wall of the blood vessel. It is similar to taking a sharp knife and cutting the surface of dried dough crust. The current shape of the cutting balloon is the typical shape of a regular angioplasty balloon except, the balloon has athrotomes or blades of a specific height mounted in the direction of the balloon and longitudinally at four equidistant points on the balloon. The other cause of falling debris in the blood stream is the multiple contacts of the intravascular procedural equipments inside the lumen of the blood vessel.

Moreover, sometimes practitioners cut into artery, causing actual tears in the artery, which will result the diffusion of blood outside the artery. This can lead to a pericardial effusion or effusion of blood around the heart pericardium. When this occurs, the chest has to be pierced with a long needle to go from the outside chest to the inside of the chest cavity to pierce the pericardial sac that surrounds the heart.

The general knowledge and acceptance with intravascular procedures is that, the less the steps, the safer and better the procedure will be. Multi steps processes will elevate the chances of scratching of the intimal wall, cuts, punctures, falling debris, and the like. All these will lead to more serious problems and complications. Therefore, most clinicians prefer "primary stenting", meaning placement of stent without the use of a cutting balloon or a pre-dilation angioplasty balloon to widen the area to be stented if it is feasible or an option.

Furthermore, most practitioners feel that the more they expand a balloon in a blood vessel (pre-dilate), the better they can pass a stent with ease. However, it could lead to an uneven tearing of the intimal wall of the artery when an angioplasty balloon is used or cutting through the vessel itself in cases where cutting balloons are used.

SUMMARY OF INVENTION

This invention is a stent that has cutting bars or blades in the direction of the balloon and longitudinally at five equidistant points along the direction of the stent's body. There are two patterns in this invention. The first pattern has five blades equidistant from the other and run longitudinally along the direction of the stent body. The other has five shorter blades equidistant from the other to constitute one set. Each set is arranged in a staggered pattern from the next set. Furthermore, the edges of stent's blades or bars are angular or beveled in order to facilitate the entry of blades into a blockage caused by calcium, plaque and/or debris.

Objects and Advantages

The new stent will reduce the multi-steps process that requires the exchange of a cutting balloon in order to place the stent in blockage area to direct placement of stent in the area. The general knowledge and acceptance with intravascular procedures is that, the less the steps, the safer and better the procedure will be. Multi-steps processes can elevate the complication and chances of scratching of intimal wall, cuts, punctures, falling debris, and the like, which ultimately can lead to more serious problems and complications. Therefore, the new stent will reduce the likelihood of small and larger plaque and debris that can be dislodged in the distal blood vessel causing flow obstruction.

The new stent will also reduce the likelihood of falling debris in the blood stream that is caused by scoring of the hard plaque and debris. The current cutting balloon has blades that have square sides. The new stent will have an angular or beveled face at the beginning and end of each blade. The angular raise will facilitate the ease of the blades into to plaque and debris. With fewer disturbances in the area, the likelihood of falling debris from the plaque will also greatly lessen.

The other cause of falling debris in the blood stream is the multiple contacts of the intravascular procedural equipments. The new stent eliminates the need to change equipment in and out of a blood vessel like the changing of equipment if a cutting balloon were used. The new stent's blades will serve the function as the cutting balloon.

Moreover, the new stent will reduce the likelihood of practitioners cutting into artery causing an intimal flap in the artery caused by over-inflation of the current cutting balloon. Using the current cutting balloon causes micro tears on the intimal wall of a blood vessel. With the new stent, the bars or blades cut while the stent body is tacking up any micro-tears and falling debris. Additionally, the chances of over-inflating, causing a serious score through the blood vessel are eliminated because the new stents has a stent pattern integrating the blades.

REFERENCE NUMERALS IN DRAWINGS

| | |
|---|---|
| 20 non-staggered blades stent | 22 inflatable balloon |
| 24 staggered blades stent | 26 non-staggered blades |
| 28 strut | 30 diameter of stent |
| 32 end of blade surface | 34 first set of staggered blades |
| 36 second set of staggered blades | 38 tubular form of stent pattern |
| 40 strut patterns integrated to side of blade | 42 blade with rounded bevel edge |
| 44 Open ended ring with arms | 46 point of attachment with beveled edge |

DESCRIPTION OF PREFERRED EMBODIMENT

Figure 18:
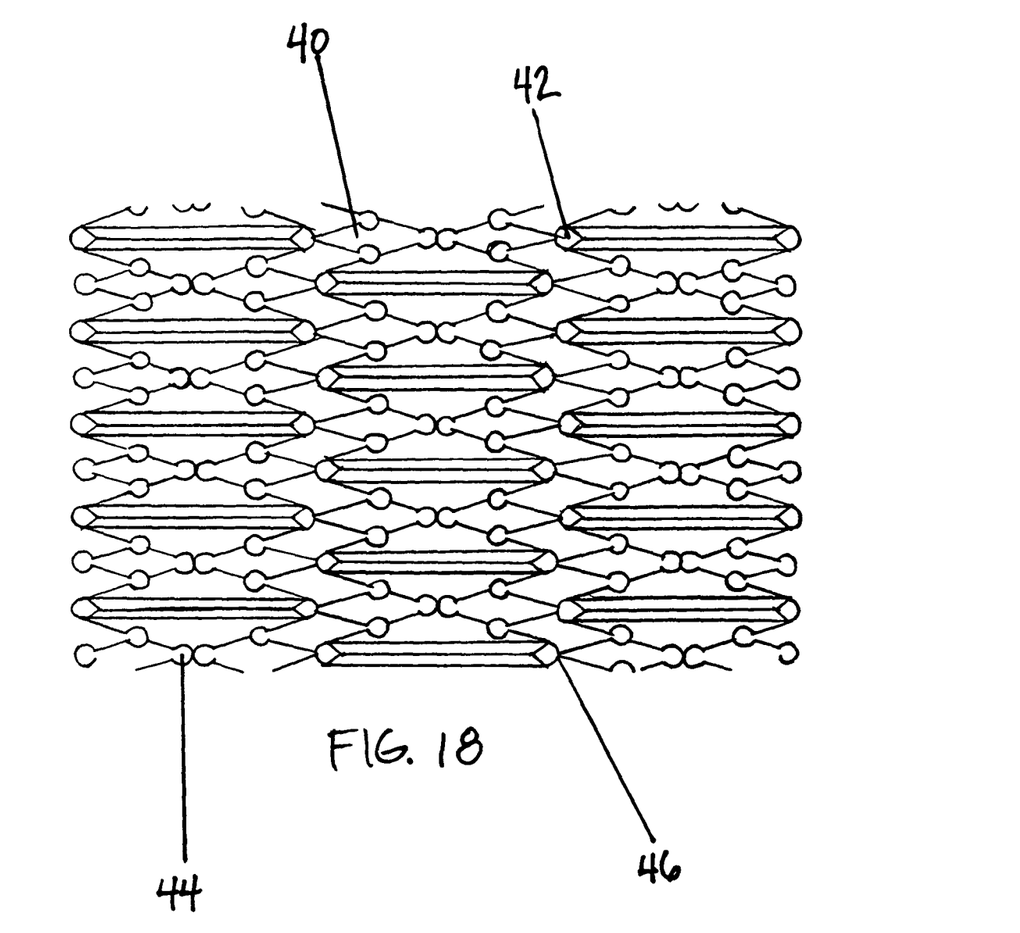
FIG. 18 Flat view of blades integrated in stent pattern.
Figure 19:
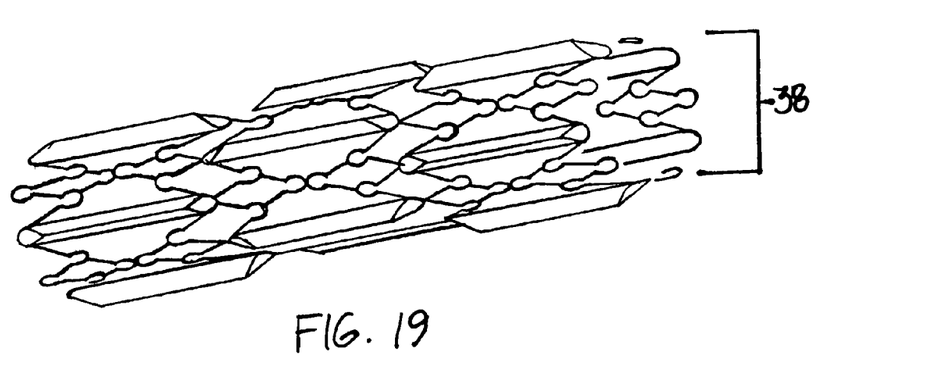
FIG. 19 Tubular view of stent pattern.

The flat view FIG. 18 consists of the blades integrated with a strut pattern. The strut pattern 40 integrates to the sides of each blade. Each strut 44 has an open ring with an edge, where each edge has an arm extending from the opening edge of the circle. At the end of each aim, another open-end circle joins. The pattern of open-ended circles and arms replicate to form an expandable, flexible pattern that integrates each blade 26. Each subsequent set of staggered blades 36 connects to the previous set of staggered blades 34 by each arm that extends from each open-ended circle to the base of each end of the blade surface 42. At the point of attachment 42, the two arms connect to the base of each blade's beveled edge 46.

The stent's material is composed of any conventional metals used in conventional stents. The strut design of stent is to the discretion of individual manufactures. However a pattern shown FIG. 18 integrates the blades in a stent pattern. The main embodiment of this invention is the blades on the stent, which exist currently in 2 patterns FIGS. 3, 4, 5, 6, 7, 8, & 9.

The stent, which has blades 20, which looks like pyramidal or triangular lines of metal bars, integrated onto the stent pattern FIG. 3, 6, 7, 8, 9. The preferred angle for the end surface of blade 26 is somewhere between 5 degrees to 45 degrees. However, angle at each beginning and end of the blades can range between 1 degree to 80 degrees FIGS. 4 & 8. These blades 20 run in the same direction as the stent's body. The blade ends 32 are beveled at an angle between 5 degrees to 45 degrees. This will facilitate the ease in crossing blockages with low resistance. This bevel shape will assist the stent to ease into place. There are two types of pattern for the new stents which exist FIGS. 3 & 6. One new stent has multiple blades FIG. 6 that are staggered by 36 degrees from each set of 5 bars or blades, and the stent FIG. 3 with blade of specific lengths. The long bars or blades that are not staggered but run longitudinally along the full length of the stent body can be used on blockages where blood vessels are almost straight or have a slight curve. The multi bar or staggered blade stent can be used on blood vessels that are more curved FIG. 6.

Figure 1:
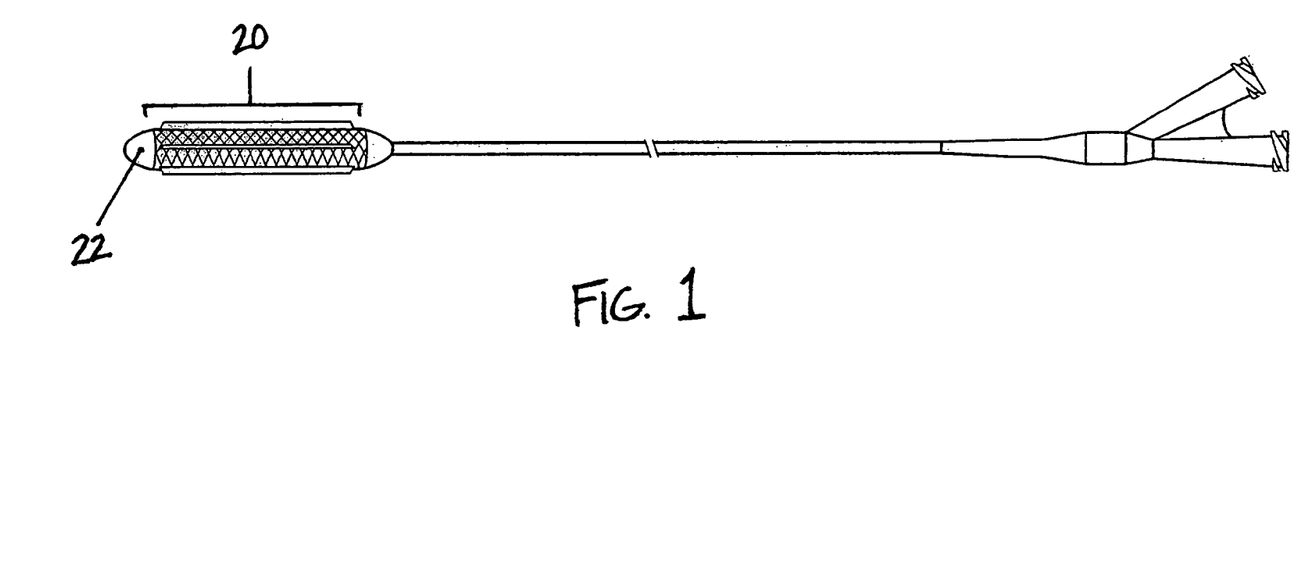
FIG. 1 Catheter, stent, and inflatable balloon ensemble for non-staggered blades stent.
Figure 2:
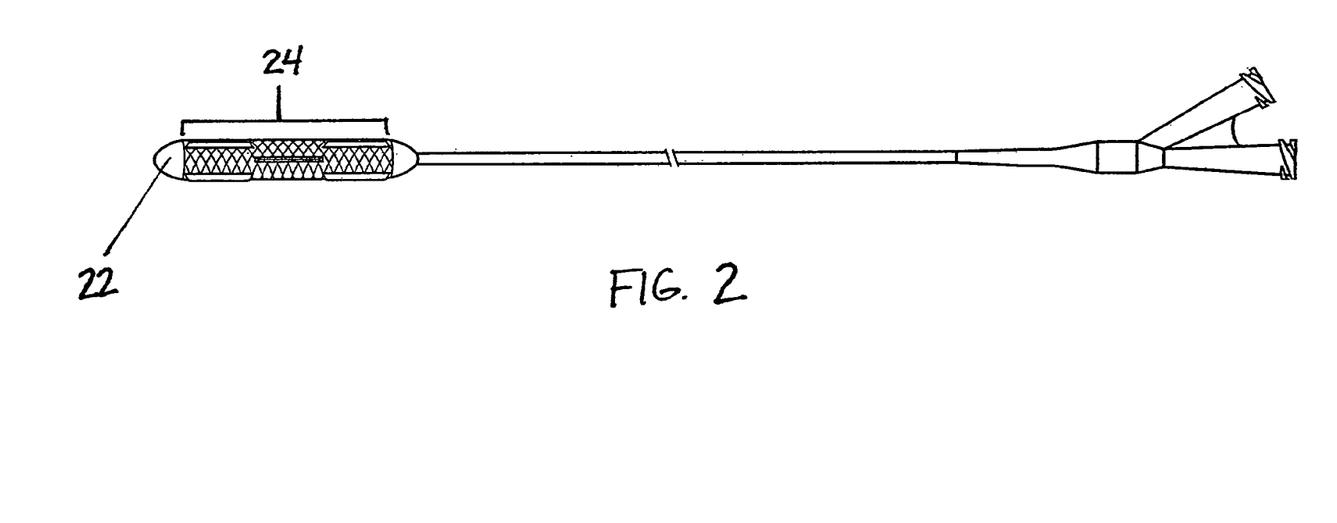
FIG. 2 Catheter, stent, and inflatable balloon ensemble for staggered blades stent.
Figures 3, 4, 5:
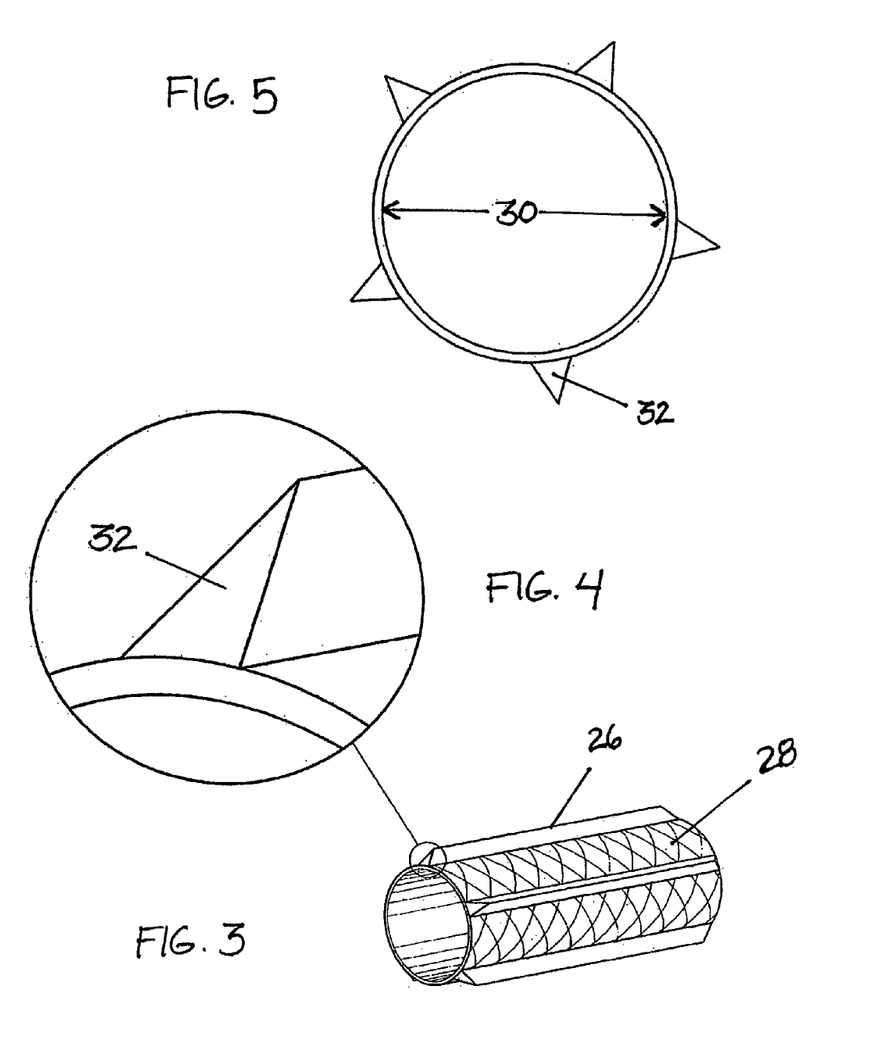
FIG. 3 Non-staggered blades stent.
FIG. 4 Exploded view of blades on stent.
FIG. 5 Bird-eye view of stent.
Figure 6:
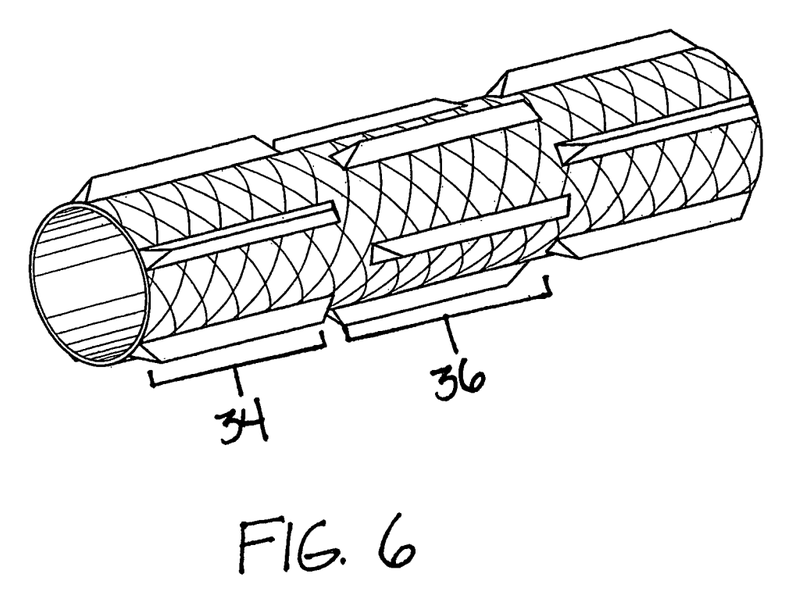
FIG. 6 Staggered blades stent.
Figure 7:
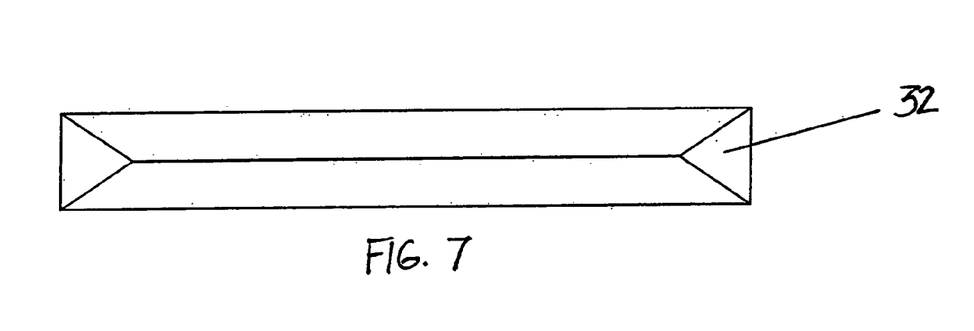
FIG. 7 Flat view of non-staggered stent and blade.
Figure 8:
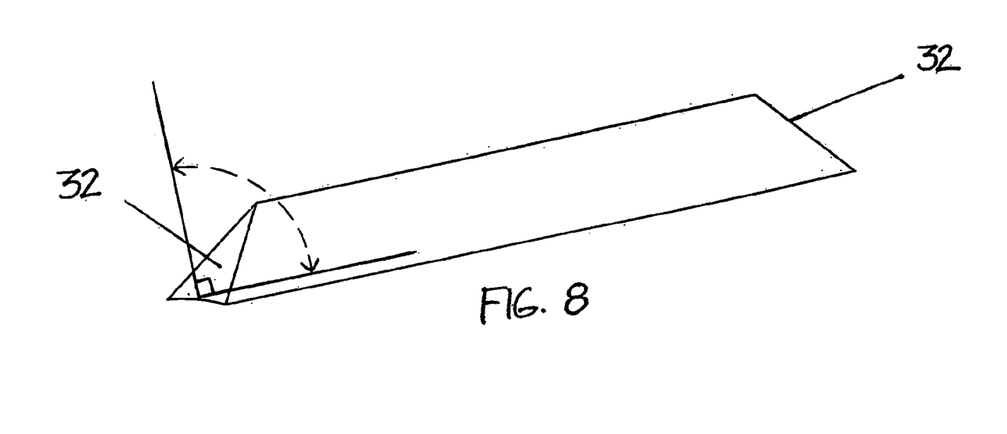
FIG. 8 View of blade, staggered or non-staggered.
Figure 9:
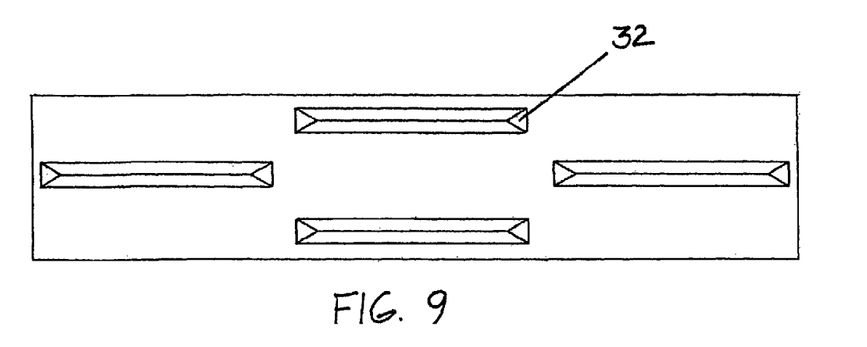
FIG. 9 Flat view of staggered stent and blade.
Figure 10:
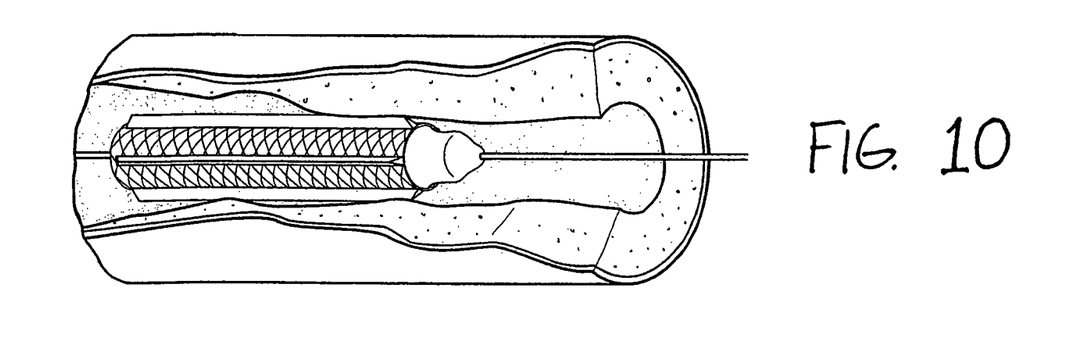
FIG. 10 Delivery of non-staggered stent to blockage.
Figure 11:
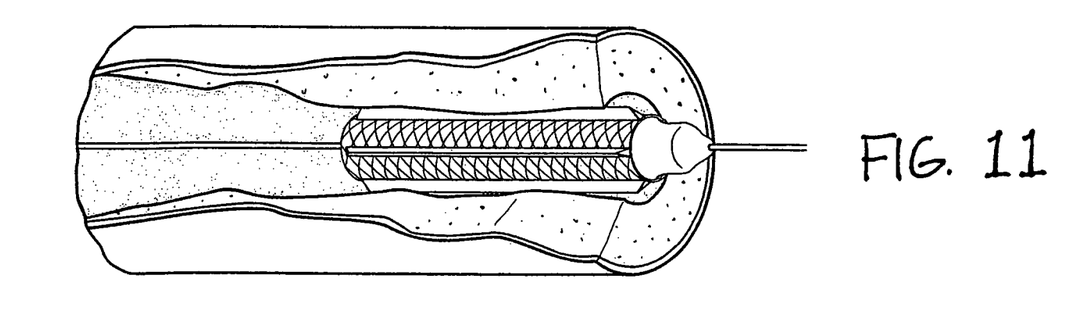
FIG. 11 Positioning of non-staggered stent in blockage.
Figure 12:
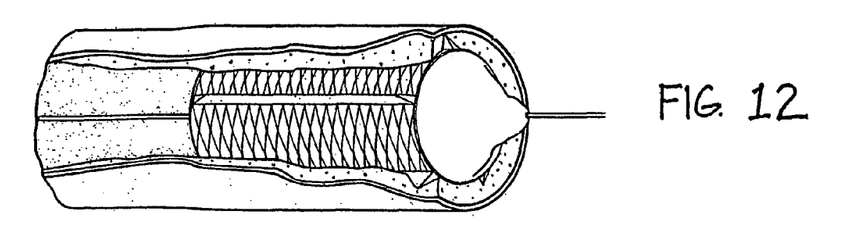
FIG. 12 Full expansion of non-staggered stent in blockage.
Figure 13:
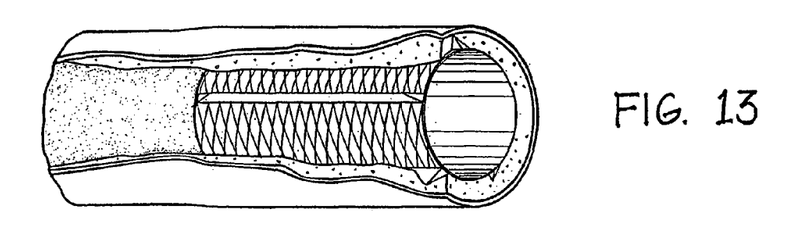
FIG. 13 View of stent after the removal of other intravascular equipment.
Figure 14:
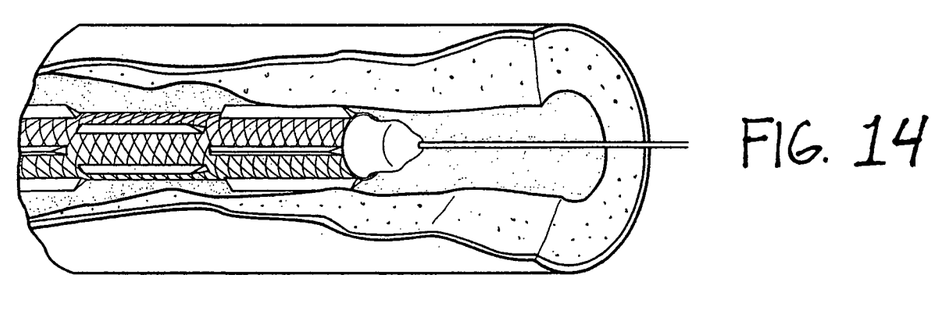
FIG. 14 Delivery of staggered stent to blockage.
Figure 15:
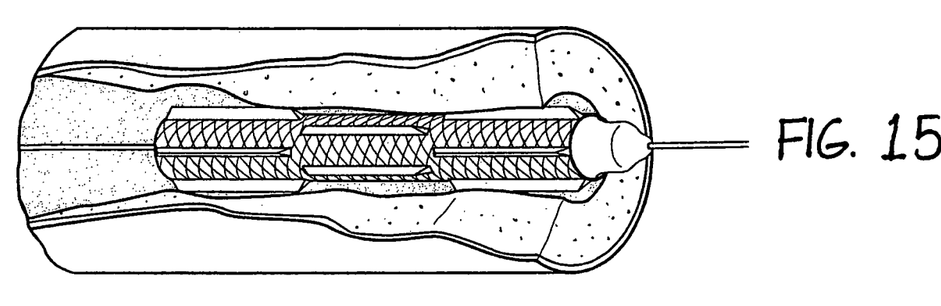
FIG. 15 Positioning of staggered stent in blockage.
Figure 16:
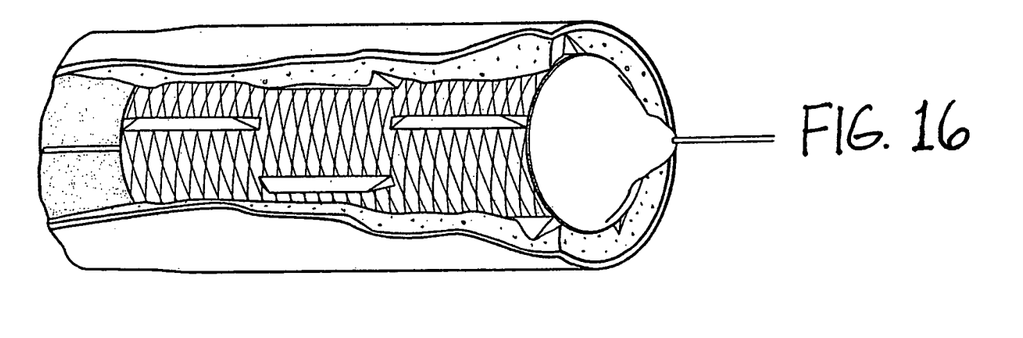
FIG. 16 Full expansion of staggered stent in blockage.
Figure 17:
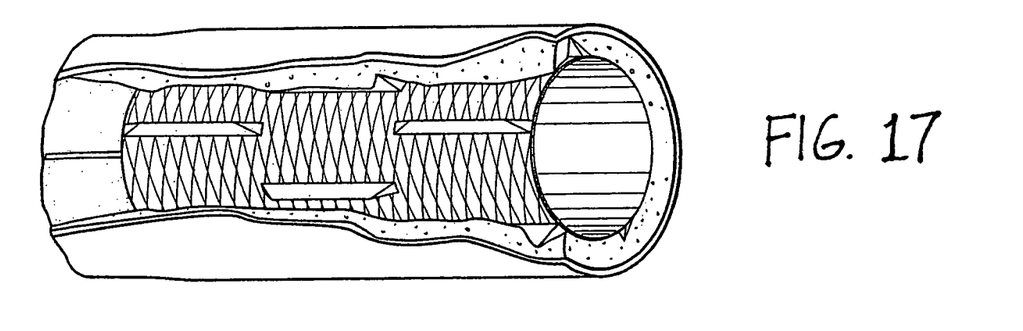
FIG. 17 View of stent after the removal of other intravascular equipment.

The shorter blades in FIGS. 6 & 9 also look like pyramidal or triangular lines of metal bars. The preferred angle for the end surface of blade 32 is somewhere between 5 degrees to 45 degrees. However, the angle of the end surface of blade 32 can range between 1 degree to 80 degrees. The shorter blades of FIGS. 6 & 9 has the first set 34 of blades that run staggered but longitudinally along the stent body with each end of each blade end 30 has an angle between 5 degrees to 45 degrees. The diameter of an un-inflated stent is approximately 0.069 inches or smaller FIG. 5. Each of the five blades 34 is set 72 degrees apart. A plurality of each set of five blades stagger the next by 36 degrees 36. This spatial orientation is optimal for scoring the plaque and debris in slightly curved blood vessels where the scoring is just enough to cut the debris so that cuts result is not too big or too small pieces of debris. However, the number of blades mounted on the stent can range from 2 to 8 sets of fives. Moreover, the arrangement of blades can be irregularly divided around the circumference of the stent FIG. 5,6. The cutting stent with continuous blades can range from 2 to eight blades running longitudinally along the body of the stent and having a beveled edge where the stent body begins and ends.

The second sets 36 of blades are circumferentially staggered by a distance that provides flexibility from the first set 34 of blades. The degree of stagger will allow the second ring of triangular bars to be evenly rotated from the first set of bars by a staggering of 26 degrees and provide flexibility in a blood vessel that is slightly curved. The blades on the second set 36 are exactly like the ones on the first set 34. However, different combinations of blade size, shape, and end are foreseeable.

This stent involves a single step in stenting procedure FIGS. 10, 11, 12, 13, 14, 15, 16, & 17. Stent's delivery is the same as the conventional process of primary stenting, which consist of the following steps. First, a guiding catheter and engaging the blood vessel is performed. A guidewire is inserted in the same fashion to extend into the distal end of the blood vessel. Next, a stent guiding catheter goes over the guidewire. Then, the bladed stent is mounted on an expandable balloon. The stent/balloon combination is passed over the guidewire and placed into the uninterrupted or pre-dilated lesion or blockage. Once the stent slid through the blockage, the balloon is inflated to a nominal atmospheric pressure by use of a balloon inflation device in the area of the blockage. While the stent is being inflated, the stent blade cuts into the intimal wall layer of the blood vessel. This scoring of the intimal wall in five points or places at 72 degrees apart will allow the plaque and debris to break evenly in the fissures it has created while the stent pattern which integrates the blades tack-up and scaffolds the freshly cut debris.

What is claimed is:

1. A stent for cutting into a blockage to wedge the stent in a blood vessel, comprising:
   a plurality of struts forming a stent body, the plurality including a space between two struts;
   one or more blades, wherein each blade includes a base with a first edge and a second edge, the first edge and the second edge attached to two or more struts such that each of the one or more blades are integral with said plurality of struts with the base extending over a portion of the space between two struts, each blade further comprising:
   a first free end extending to a second free end, wherein the first free end is beveled forming a first beveled end and the second free end is beveled forming a second beveled end, the first beveled end and the second beveled end each at an acute angle with respect to the base of the blade;
   a cutting edge disposed on the blade, wherein the cutting edge is positioned between the first beveled end and the second beveled end and the cutting edge is distally opposed to the base of the blade,
   wherein the cutting edge of the blade is linear and oriented substantially parallel to a longitudinal axis centered in a lumen of the stent body,
   wherein the longitudinal axis centered in the lumen of the stent body extends from a proximal opening of the stent body to a distal opening of the stent body, and
   wherein the first beveled end and the second beveled end of the blade is configured for entrance into the blockage of the blood vessel upon expansion and implantation of the stent into the blood vessel and the cutting edge disposed on the blade is configured to cut into the blockage to wedge the stent in the blood vessel.

2. The stent of claim 1, wherein the one or more blades create in a direction of the longitudinal axis fissures and scores in the blood vessel when implanting the one or more blades into the blood vessel.

3. The stent of claim 1, wherein the one or more blades create staggered longitudinal fissures when the blood vessel is scored by the expanding of the stent body.

4. The stent of claim 1, wherein the one or more blades comprise 5 to 8 blades.

5. The stent of claim 4, wherein the one or more blades create staggered longitudinal fissures in the blood vessel in a direction of the longitudinal axis of the lumen of the stent body.

6. The stent of claim 4, wherein the one or more blades create longitudinal fissures 72 degrees apart circumferentially about the blood vessel.

7. The stent of claim 6, wherein the one or more blades are joined together by multiple connections of the plurality of struts.

8. The stent of claim 4, wherein the one or more blades have varying distances of separation from each other in the longitudinal direction of the lumen of the stent body.

9. The stent of claim 4, wherein the one or more blades are equidistant from each other in the longitudinal direction of the lumen of the stent body.

10. The stent of claim 1, wherein each of the plurality of blades has a blade length that is at least one third a length of the stent.

11. The stent of claim 1 further comprising one of the first beveled end of the blade and the second beveled end of the blade positioned at one of the proximal opening of the stent body and the distal opening of the stent body.

12. The stent of claim 1, wherein each strut comprises an open circle with an arm extending from at least one end of the open circle.

13. A stent, comprising:
   a pattern of struts forming a stent body, wherein the pattern includes a space between two or more struts; and
   blades, wherein each blade comprises a bottom edge, a top linear cutting edge, the bottom edge and the top linear cutting edge positioned between a first beveled free end and a second beveled free end, the first beveled free end including a first bottom edge transverse to the top linear cutting edge, and the second beveled free end including a second bottom edge transverse to the top linear cutting edge, wherein the bottom edge is connected to the stent body such that each blade is integral with said struts for cutting into body tissues,
   wherein the bottom edge of each blade is connected to two or more struts including a portion of the bottom edge spanning a portion of the space between two or more struts of the pattern, the blades are linear and oriented substantially parallel to a longitudinal axis of a lumen of the stent and, when the stent is viewed along the longitudinal axis of the lumen of the stent, the blades are positioned substantially symmetrically around a circumference of the stent, wherein the longitudinal axis of the lumen of the stent is centered in the stent and extends from a proximal opening of the stent to a distal opening of the stent and one of the first beveled free end and the second beveled free end of one or more blades is positioned at one of the proximal opening and the distal opening of the stent, and wherein the first beveled free end and the second beveled free end of each blade is configured for entrance into the blockage of the blood vessel upon expansion and implantation of the stent into the blood vessel and the top linear cutting edge disposed on each blade between the first beveled free end and the second beveled free end is configured to cut and wedge the stent in a blood vessel.

14. The stent of claim 13, wherein each strut comprises an open circle with an arm extending from at least one end of the open circle.

15. A stent, comprising:
   a plurality of struts forming a stent body, wherein the plurality includes a space between two or more struts; and
   a plurality of blades for cutting into body tissues, each blade integral with said plurality of struts and each blade extending from a first free end to a second free end and each blade including a base with a first edge and a second edge, the first edge and the second edge attached to one or more struts of the stent body with the base positioned over the space between two or more struts of the plurality and further comprising:

with the base extending over a portion of the space between two struts including a portion of the bottom edge spanning a portion of the space between two or more struts of the pattern a cutting edge distally opposed to the base, the cutting edge extending from the first free end to the second free end, wherein the first free end is beveled to form a first beveled blade end and the second free end is beveled to form a second beveled blade end, the first beveled end and the second beveled end each at an acute angle with respect to the base of the blade, wherein the cutting edge of each blade is linear and oriented substantially parallel to a longitudinal axis of a lumen of the stent, the first beveled blade end including a first bottom edge transverse to the longitudinal axis of the lumen and the second beveled blade end including a second bottom edge transverse to the longitudinal axis of the lumen, wherein the longitudinal axis is centered in the lumen of the stent and extends from a proximal opening of the stent to a distal opening of the stent, and wherein one of the first beveled end of the blade and the second beveled end of one blade is located at one of the proximal opening of the stent and the distal opening of the stent, the first beveled blade end and the second beveled blade end are configured for entrance into the blockage of the blood vessel upon expansion and implantation of the stent into a blood vessel and the cutting edge is configured to cut and wedge the stent into a blood vessel.

16. The stent of claim 15, wherein each blade of the plurality of blades is positioned equidistant from one another.

17. The stent of claim 15, wherein the plurality of blades comprises a first set of blades that is arranged in a staggered pattern from a second set of blades.

18. The stent of claim 15 further comprising the first beveled free end and the second beveled free end each at an acute angle with respect to the bottom edge of the blade.

19. The stent of claim 15, wherein each strut comprises an open circle with an arm extending from at least one end of the open circle.

* * * * *